(12) United States Patent
Takeuchi et al.

(10) Patent No.: US 11,534,519 B2
(45) Date of Patent: Dec. 27, 2022

(54) PTP BLISTER SHEET, AND PTP BLISTER PACK FORMED FROM SAME

(71) Applicant: DAI NIPPON PRINTING CO., LTD., Tokyo (JP)

(72) Inventors: Naoya Takeuchi, Tokyo (JP); Taeko Matsushita, Tokyo (JP); Koki Akutsu, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 85 days.

(21) Appl. No.: 15/306,393

(22) PCT Filed: May 29, 2015

(86) PCT No.: PCT/JP2015/065502
§ 371 (c)(1),
(2) Date: Oct. 24, 2016

(87) PCT Pub. No.: WO2015/182736
PCT Pub. Date: Dec. 3, 2015

(65) Prior Publication Data
US 2017/0043045 A1 Feb. 16, 2017

(30) Foreign Application Priority Data

May 30, 2014 (JP) .............................. JP2014-111861

(51) Int. Cl.
*A61L 9/014* (2006.01)
*B32B 27/00* (2006.01)
(Continued)

(52) U.S. Cl.
CPC ............. *A61L 9/014* (2013.01); *B01J 20/045* (2013.01); *B01J 20/103* (2013.01); *B01J 20/261* (2013.01);
(Continued)

(58) Field of Classification Search
None
See application file for complete search history.

(56) References Cited

U.S. PATENT DOCUMENTS

| 6,503,962 B1 * | 1/2003 | Mouri | ...................... C08K 9/04 |
| | | | 428/905 |
| 2010/0136271 A1 * | 6/2010 | Ishihara | ................ B29C 51/002 |
| | | | 428/36.7 |

(Continued)

FOREIGN PATENT DOCUMENTS

| JP | 6-225927 | 8/1994 |
| JP | 2538487 B | 9/1996 |

(Continued)

OTHER PUBLICATIONS

JP 2006-334819 English Machine Translation (Year: 2006).*

(Continued)

*Primary Examiner* — Alicia Chevalier
*Assistant Examiner* — Elaine M Vazquez
(74) *Attorney, Agent, or Firm* — Hamre, Schumann, Mueller & Larson, P.C.

(57) ABSTRACT

To provide a PTP blister sheet exhibiting a high adsorption effect over prolonged periods, and a PTP blister pack formed from it. A PTP blister sheet having at least a gas barrier layer and an odor adsorption layer, wherein the odor adsorption layer comprises a heat-sealable resin containing an odor adsorption agent, and the odor adsorption agent is formed by a chemical adsorption agent supported on an inorganic porous body, and a PTP blister pack formed from it.

8 Claims, 2 Drawing Sheets

(51) Int. Cl.

| | |
|---|---|
| *B32B 27/18* | (2006.01) |
| *B65D 75/32* | (2006.01) |
| *B32B 27/32* | (2006.01) |
| *B32B 27/34* | (2006.01) |
| *B32B 7/12* | (2006.01) |
| *B29C 39/00* | (2006.01) |
| *B32B 27/30* | (2006.01) |
| *B01J 20/32* | (2006.01) |
| *B01J 20/26* | (2006.01) |
| *B01J 20/04* | (2006.01) |
| *B01J 20/28* | (2006.01) |
| *B65D 65/40* | (2006.01) |
| *B01J 20/10* | (2006.01) |
| *B32B 27/06* | (2006.01) |
| *B65D 75/36* | (2006.01) |

(52) U.S. Cl.
CPC ....... *B01J 20/262* (2013.01); *B01J 20/28026* (2013.01); *B01J 20/3204* (2013.01); *B01J 20/3246* (2013.01); *B01J 20/3248* (2013.01); *B29C 39/00* (2013.01); *B32B 7/12* (2013.01); *B32B 27/00* (2013.01); *B32B 27/06* (2013.01); *B32B 27/18* (2013.01); *B32B 27/304* (2013.01); *B32B 27/306* (2013.01); *B32B 27/32* (2013.01); *B32B 27/34* (2013.01); *B65D 65/40* (2013.01); *B65D 75/32* (2013.01); *B65D 75/36* (2013.01); *B32B 2250/24* (2013.01); *B32B 2255/10* (2013.01); *B32B 2255/26* (2013.01); *B32B 2264/102* (2013.01); *B32B 2264/12* (2013.01); *B32B 2307/31* (2013.01); *B32B 2307/726* (2013.01); *B32B 2307/7242* (2013.01); *B32B 2307/732* (2013.01); *B32B 2307/758* (2013.01); *B32B 2439/80* (2013.01)

(56) References Cited

U.S. PATENT DOCUMENTS

2013/0168270 A1* 7/2013 Koizumi ................. B32B 1/02
                                                     206/204
2014/0363655 A1* 12/2014 Yoshida ................. B32B 27/34
                                                     428/220

FOREIGN PATENT DOCUMENTS

| JP | 2006-334784 | | 12/2006 |
| JP | 2006-334819 | | 12/2006 |
| JP | 2006346888 A | * | 12/2006 |
| JP | 2012-206776 | | 10/2012 |
| JP | 2013-006410 | | 1/2013 |
| WO | 2010/134137 | | 11/2010 |

OTHER PUBLICATIONS

JP H06-225927 English Machine Translation (Year: 1994).*
JP 2006-346888 English Machine Translation (Year: 2006).*
International Preliminary Report on Patentability issued in International Application No. PCT/JP2015/065502, dated Dec. 6, 2016, 6 pages.
Office Action issued for the corresponding Japanese Patent Application No. 2018-133321, dated May 28, 2019, 10 pages including machine translation.
Office Action issued for the corresponding Japanese Patent Application No. 2018-133321, dated Sep. 10, 2019, 10 pages including machine translation.

* cited by examiner

PTP BLISTER SHEET, AND PTP BLISTER PACK FORMED FROM SAME

TECHNICAL FIELD

The present invention relates to a PTP blister sheet and to a PTP blister pack formed from it, and specifically to a PTP blister sheet having a deodorant property against odors emitted from contents, and to a PTP blister pack formed from it.

BACKGROUND ART

Among packaging materials, there have been proposed packaging materials that enclose odor adsorption agents that adsorb odors (PTL 1). In such packaging materials, an odor adsorption agent such as synthetic zeolite or active carbon is kneaded in a resin material.

However, because such packaging materials adsorb not only odors but also moisture in the air, it has not been possible to obtain adequate odor absorbing power. Desorption of once-adsorbed odors is another problem that is faced.

CITATION LIST

Patent Literature

[PTL 1] Japanese Patent Publication No. 2538487

SUMMARY OF INVENTION

Technical Problem

It is an object of the present invention to solve these problems and provide a PTP blister sheet that can efficiently adsorb odors without desorption of odors that have already been adsorbed, and that exhibits a high adsorption effect for prolonged periods without reduction in odor adsorption capacity, as well as a PTP blister pack formed from it.

Solution to Problem

As a result of much research, the present inventors have found that the aforementioned object can be achieved by a PTP blister sheet having at least a gas barrier layer and an odor adsorption layer, wherein the odor adsorption layer comprises a heat-sealable resin containing an odor adsorption agent, and the odor adsorption agent is formed by a chemical adsorption agent supported on an inorganic porous body, as well as a PTP blister pack formed from it.

The present invention has the following features.

(1) A PTP blister sheet having at least a gas barrier layer and an odor adsorption layer, wherein the odor adsorption layer comprises a heat-sealable resin containing an odor adsorption agent, and the odor adsorption agent is formed by a chemical adsorption agent supported on an inorganic porous body.

(2) A PTP blister sheet according to (1) above, wherein the odor adsorption layer contains the odor adsorption agent in a range of from 0.5 mass % to 30 mass %.

(3) A PTP blister pack comprising a PTP blister sheet according to (1) or (2) above.

Advantageous Effects of Invention

The PTP blister sheet of the invention, having an odor adsorption layer, can adsorb odors emitted by the contents of the blister pack and odors emitted by the pack itself, and thus provide a deodorant effect.

Furthermore, the PTP blister sheet of the invention has a gas barrier layer and an odor adsorption layer having a specific construction, layered in that order from the outer side to the inner side of the pack. With this construction, the sheet of the invention has excellent moldability and can efficiently adsorb odors in the pack over prolonged periods.

Thus, the sheet of the invention is especially suitable as a PTP blister for packing of drugs containing odor-emitting components, and it can reduce odors while also reducing unpleasantness experienced upon opening or ingesting.

In addition, since the odor adsorption layer comprises a heat-sealable resin containing an odor adsorption agent with a specific construction, it has both a heat sealing property and an odor adsorbing property, and therefore reduced material cost and fewer process steps, and excellent productivity.

Furthermore, according to the invention, the odor adsorption agent has a chemical adsorption agent supported on an inorganic porous body, and therefore odor adsorption can be efficiently exhibited without desorption of odors that have been adsorbed by the chemical adsorption effect.

In addition, unlike physical adsorption agents wherein odors and water vapor are simultaneously adsorbed at the adsorption site, in the chemical adsorption agent of the invention, the odors bind to specific functional groups, and hence there is less of an effect by various substances that lower the odor adsorption capacity, such as water vapor.

DESCRIPTION OF EMBODIMENTS

The invention will now be explained in greater detail.

<Multilayer Structure of PTP Blister Sheet of the Invention>

Figure 1:
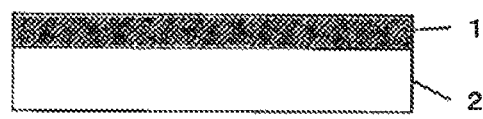
FIG. 1 is a schematic cross-sectional diagram showing an example of the multilayer structure of a PTP blister sheet of the invention.

FIG. 1 is a schematic cross-sectional diagram showing an example of the multilayer structure of a PTP blister sheet of the invention. As shown in FIG. 1, the PTP blister sheet of the invention has a gas barrier layer 1 and an odor adsorption layer 2 that are layered.

Figure 2:
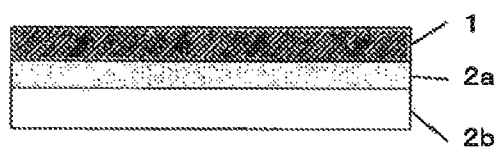
FIG. 2 is a schematic cross-sectional diagram showing an example of the multilayer structure of a PTP blister sheet of the invention.

As shown in FIG. 2, the odor adsorption layer 2 may have a multilayer structure comprising two layers 2a, 2b. The type of heat-sealable resin and the content of the odor adsorption agent may be different in the different layers. For example, one of the two layers, such as the layer 2a on the side facing the gas barrier layer 1, may comprise a heat-sealable resin containing an odor adsorption agent, while the layer 2b on the side that is the innermost layer may comprise a heat-sealable resin containing no odor adsorption agent. If the layer 2b contains no odor adsorption agent, the seal strength of the pack can be improved.

Conversely, if the layer 2a contains no odor adsorption agent while the layer 2b contains an odor adsorption agent, the interlayer bonding strength can be improved.

Furthermore, while not shown, the odor adsorption layer may consist of 3 or more layers. Here as above, the type of heat-sealable resin and the content of the odor adsorption agent may be different in the different layers. For example, with a three-layer structure of: layer containing no odor adsorption agent (outer layer)/layer containing odor adsorption agent (intermediate layer)/layer containing no odor adsorption agent (inner layer), it is possible to increase the seal strength and interlayer bonding strength.

Figure 3:
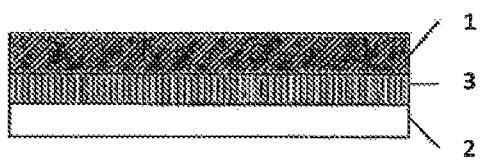
FIG. 3 is a schematic cross-sectional diagram showing an example of the multilayer structure of a PTP blister sheet of the invention.

Furthermore, as shown in FIG. 3, a moisture absorption layer that adsorbs moisture may be provided in the pack, between the gas barrier layer and the odor adsorption layer.

<Gas Barrier Layer>

According to the invention, the film composing the gas barrier layer is not particularly restricted, and any publicly known or commercially available gas barrier film may be applied so long as it can inhibit oxygen permeation or water vapor permeation from the outside world.

Specific gas barrier films that may be used include resin films made of resins such as polyethylene terephthalate (PET), polybutylene terephthalate, polyvinyl chloride, polyvinylidene chloride, polyethylene naphthalate, polypropylene, polyamide, polyimide, polyvinyl alcohol, ethylene/vinyl alcohol copolymers or the like, or vapor deposition films in which a vapor deposition film such as a silica vapor deposition film or alumina vapor deposition film is provided on at least one side of a desired base film, or metal foils such as aluminum foil, with no limitation to these. Among such films, resin films made of polypropylene, polyvinyl chloride or polyvinylidene chloride, or aluminum foil, are preferred for use.

When an aluminum foil is used as the gas barrier film, it preferably has a two-layer structure with a base film layered on one side thereof. Using a resin film made of polyester, polyamide or polyolefin as such a base film is particularly preferred from the viewpoint of mechanical strength and excellent pinhole resistance.

The resin film used may be a monolayer or multilayer film formed using a film forming method such as an extrusion method, cast molding method, T-die method, shaving method or inflation method.

According to the invention, the film thickness of the gas barrier film is preferably 3 to 350 μm and more preferably 5 to 300 μm.

<Odor Adsorption Layer>

Odor Adsorption Agent

According to the invention, the odor adsorption layer is made of a heat-sealable resin containing an odor adsorption agent. The odor adsorption agent has an adsorption function for odorous substances emitted by the contents of the pack or the pack itself, with a chemical adsorption agent supported on an inorganic porous body. The supporting method used may be a publicly known or commonly used supporting method, and for example, a solution containing the chemical adsorption agent, as described below, may be impregnated into an inorganic porous body and dried to support it.

By using a chemical adsorption agent supported on an inorganic porous body in the odor adsorption layer of the invention, it is possible to drastically increase the odor adsorption capacity per mass of the chemical adsorption agent. This allows the amount of chemical adsorption agent added to the heat-sealable resin to be reduced, so that excellent film formability, moldability and heat sealing properties required for a PTP blister sheet can be maintained.

Inorganic Porous Body

According to the invention, the inorganic porous body used may be any desired inorganic compound having a plurality of pores in the surface, and examples include zeolite, silicon dioxide, silicates, active carbon, titania, inorganic phosphates such as calcium phosphate, alumina, aluminum hydroxide, magnesium hydroxide, and mixtures of the foregoing. Particularly preferred are aluminum hydroxide, zeolite, silicates and silicon dioxide from the viewpoint of having an effective porous state for the size of the substances to be adsorbed, and of safety.

These may be of any desired outer shape such as spherical, rod-shaped or ellipsoid, or they may be in any form such as powder, masses or granules, but they are preferably in powder form from the viewpoint of film formability of the odor adsorption layer, and a uniform kneading property in the heat-sealable resin.

The inorganic porous body may be appropriately selected as one having a desired size for the purpose of use, but according to the invention it is most preferably one with a mean particle size of 0.01 μm to 10 μm. If the mean particle size is smaller than 0.01 μm, the inorganic porous body will tend to aggregate and dispersibility of the inorganic porous body in the heat-sealable resin will tend to be inhibited, while if the mean particle size is 10 μm or greater, it may not be possible to obtain high film formability of the heat-sealable resin or an increased amount of addition of the odor adsorption layer in the heat-sealable resin, potentially making it impossible to obtain a sufficient deodorant effect. Furthermore, it can result in irregularities being produced in the film surface, impairing the film formability.

The mean particle size is the value measured by a dynamic light scattering method.

Chemical Adsorption Agent

According to the invention, a chemical adsorption agent is a compound having a reactive functional group that undergoes chemical reaction with and binds to odorous substances to be removed, and that can be supported on an inorganic porous body.

When odorous substances to be removed are acidic substances such as carboxylic acids, hydrogen sulfide or mercaptanes, there may be used a chemical adsorption agent which is a compound having as the reactive functional group a basic functional group such as hydroxyl, or a hydroxide such as sodium hydroxide, potassium hydroxide, magnesium hydroxide or iron hydroxide, a carbonate such as sodium carbonate, sodium hydrogencarbonate or calcium carbonate, a hydrogen carbonate, an amino group-containing compound such as a polyamine such as alkylamine or tetramethylenediamine, or ethanolamine, piperidine or the like, or an amide group-containing compound such as 2-acrylamide-2-methylpropanesulfonic acid.

Also, when the odorous substances to be removed are basic substances such as ammonia or amines, there may be used a chemical adsorption agent which is a compound having an acidic functional group as the reactive functional group, examples of which include phosphoric acid, sulfonic acid, carboxylic acid and their metal salts.

When the odorous substances to be removed are aldehydes, it is most preferred to use an amino group-containing compound.

By using an amphoteric substance, for example, a metal oxide such as zinc oxide, as the chemical adsorption agent, it is possible to adsorb both acidic and basic substances.

The adsorption mechanism of the odor adsorption agent for odorous substances will now be explained in further detail using the concrete examples of FIGS. 4(a) to (c), with the understanding that the invention is not limited thereto.

When the odorous substances are acidic odorous substances, the odor adsorption agent used may be, for example, one having a compound with a hydroxyl group supported on an inorganic porous body, as shown in FIG. 4(a). The carboxyl groups and hydroxyl groups will thus undergo chemical reaction and bond, so that the odorous substances are adsorbed.

Figure 4:
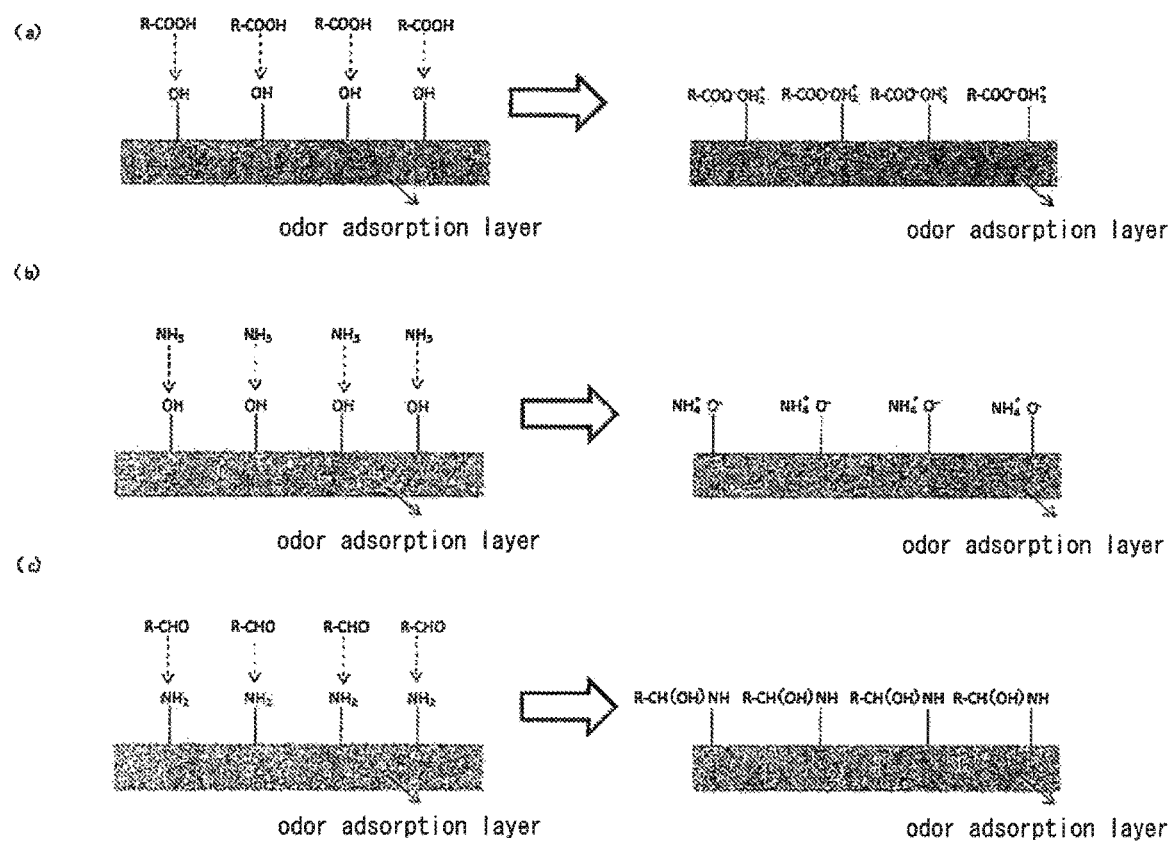
FIG. 4 is a diagram showing an adsorption mechanism for odorous substances by an odor adsorption agent.

Also, when the odorous substance is ammonia, the odor adsorption agent used may be, for example, one having a compound with a phosphate group supported on an inorganic porous body, as shown in FIG. 4 (b). The ammonia and phosphate groups will thus undergo chemical reaction and bond, so that the odorous substance is adsorbed.

Also, when the odorous substances are aldehydes, the odor adsorption agent used may be, for example, one having a compound with amino groups supported on an inorganic porous body, as shown in FIG. 4(c). The aldehyde groups and amino groups will thus undergo chemical reaction and bond, so that the odorous substances are adsorbed.

Heat-Sealable Resin

According to the invention, there are no particular restrictions on the heat-sealable resin used to form the odor adsorption layer, and any publicly known or commercially available polyolefin-based resin having a heat sealing property may be used.

Such polyolefin-based resins include polyethylenes such as low-density polyethylene (LDPE), medium-density polyethylene (MDPE), high-density polyethylene (HDPE) and straight-chain (linear) low-density polyethylene (LLDPE), polypropylene, ethylene-vinyl acetate copolymer, ethylene-ethyl acrylate copolymer, ethylene-acrylic acid copolymer, ethylene-methacrylic acid copolymer, ethylene-methyl methacrylate copolymer, ethylene-propylene copolymer, methylpentene polymer, acid-modified polyolefin-based resins, and mixtures of these resins, with no limitation to these resins.

Also, small amounts of an antioxidant, anti-blocking agent or the like may be employed in the film as an additive. LLDPE and LDPE are particularly preferred for use since they exhibit excellent heat sealing properties and odor adsorbing properties when containing odor adsorption agents.

Formation of Odor Adsorption Layer

According to one mode of the invention, the odor adsorption layer has a monolayer structure composed of a resin composition obtained by kneading an odor adsorption agent in a heat-sealable resin. The odor adsorption agent may be homogeneously dispersed in the layer. Also, for example, it may be dispersed with an increasing concentration gradient from the surface of the innermost layer side toward the surface facing the gas barrier layer, as such a construction will improve the heat sealing property. Conversely, it may be dispersed with a decreasing concentration gradient from the surface of the innermost layer side toward the surface facing the gas barrier layer, as such a construction will improve the interlayer bonding strength.

According to another mode, the odor adsorption layer has a multilayer structure with two or more layers, each layer being composed of a resin composition each with a different amount of addition of the odor adsorption agent. The structure may also include a layer consisting only of a heat-sealable resin without an odor adsorption agent.

The amount of odor adsorption agent added can exhibit a deodorant effect at 0.1 mass % or greater with respect to the mass of the odor adsorption layer as a whole, but in order to obtain a satisfactory deodorant effect it is preferably 0.5 mass % or greater and more preferably 1 mass % or greater. On the other hand, in order to obtain satisfactory film formability and moldability, the amount of odor adsorption agent added is preferably no greater than 30 mass %. In addition, in order to obtain a satisfactory heat sealing property, the amount of odor adsorption agent added is more preferably no greater than 15 mass %.

Film formation can be achieved if the layer thickness of the odor adsorption layer as a whole is 5 μm or greater, but in order to obtain satisfactory film formability, moldability, heat sealing properties and odor adsorbing properties, it is preferably 10 μm to 200 μm.

The method for kneading the odor adsorption agent in the heat-sealable resin may be a publicly known or commonly employed kneading method. For example, a pellet-like master batch may be prepared by dispersing the odor adsorption agent in the heat-sealable resin, and the batch dispersed again in the heat-sealable resin, as a so-called master batch-type blend process, to allow even easily aggregating odor adsorption agents to be homogeneously dispersed.

According to the invention, the method of layering the odor adsorption layer is not particularly restricted, and the resin composition that is to form the layer may be layered by extrusion coating on the gas barrier layer, via a bonding layer, depending on the case. For extrusion coating, first the resin composition is heated to melting and spread out in the necessary widthwise direction with a T-die for extrusion into a curtain, the molten resin is allowed to flow over the gas barrier layer and sandwiched between a rubber roll and a cooled metal roll, for simultaneous formation of an odor adsorption layer and bonding and layering with the gas barrier layer.

Also a film made of the resin or resin composition may be formed, and laminated with the gas barrier layer via a bonding layer, by dry lamination, non-solvent lamination, sand lamination or the like.

The method of forming the film in this case may be a publicly known or commonly used film forming method, and for example, when an inflation method is used as the film forming method, the melt flow rate (MFR) of the heat-sealable resin forming the odor adsorption layer is preferably 0.2 to 4 g/10 min and more preferably 0.2 to 3 g/10 min, when the odor adsorption layer is a monolayer. An MFR of less than 0.2 g/10 min or of 4.0 g/10 min or greater is not effective from the viewpoint of suitability for working.

Also, when the odor adsorption layer is a multilayer such as for example, "layer containing no odor adsorption agent (outer layer)/layer containing an odor adsorption agent (intermediate layer)/layer containing no odor adsorption agent (inner layer)", the MFR of the resin used in the layer containing the odor adsorption agent will not affect the working surface even if applied to 0.2-10 g/10 min (190° C.).

Throughout the present specification, the MFR is the value measured by a method according to JIS K7210.

<Layering>

According to one mode of the invention, layering with formation of a bonding layer between the gas barrier layer and odor adsorption layer can yield a PTP blister sheet of the invention having a gas barrier layer, bonding layer and odor adsorption layer in that order.

In this sheet, the bonding layer may be a layer of a dry laminating bonding agent, a non-solvent laminating bonding agent or the like.

When a dry laminating bonding agent is to be used as the bonding layer, a bonding agent dispersed or dissolved in a solvent is coated and dried onto one film, while the other film is layered over it, after which it is aged at 30 to 120° C. for from several hours to several days, to harden the bonding agent and form a layering.

When a non-solvent laminating bonding agent is to be used, the bonding agent itself, without being dispersed or dissolved in a solvent, is coated and dried onto one film, while the other film is layered over it, after which it is aged at 30 to 120° C. for from several hours to several days, to harden the bonding agent and form a layering.

These bonding agents may be thermosetting, ultraviolet curing, electron beam curable, or the like. Such bonding agents may be polyvinyl acetate-based bonding agents such as polyvinyl acetate or vinyl-ethylene acetate copolymers, polyacrylic acid-based bonding agents composed of a copolymer of polyacrylic acid with polystyrene, polyester, polyvinyl acetate or the like, cyano acrylate-based bonding agents, ethylene copolymer-based bonding agents composed of a copolymer of ethylene with a monomer such as vinyl acetate, ethyl acrylate, acrylic acid or methacrylic acid, cellulosic bonding agents, polyurethane-based bonding agents, polyester-based bonding agents, polyamide-based bonding agents, polyimide-based bonding agents, polyolefin-based bonding agents, amino resin-based bonding agents composed of urea resins, melamine resins or the like, phenol resin-based bonding agents, epoxy-based bonding agents, reactive (meth)acrylic-based bonding agents, elastomeric bonding agents made of chloroprene rubber, nitrile rubber, styrene-butadiene rubber or the like, silicone-based bonding agents, and inorganic bonding agents composed of alkali metal silicates, low-melting-point glass or the like.

Furthermore, the bonding agent may be in aqueous, solution, emulsion or dispersion form, and with the character of a film, sheet, powder, solid or the like, and the bonding mechanism may be by chemical reaction, solvent volatilization, heat-fusion, thermocompression, or the like.

The bonding layer is formed by applying the bonding agent by roll coating, gravure roll coating, kiss coating or the like, the coating coverage being preferably about 0.1 to 10 g/m² (dry state). If the coating coverage of the bonding agent is within this range it will be possible to obtain satisfactory adhesion.

According to another mode of the invention, the films forming the gas barrier layer and odor adsorption layer may be layered by sand lamination. In this case, for the bonding layer there may be used any desired resin that can be hot melted and applied with an extruder. Specifically, the resins mentioned above as heat-sealable resins are suitable for use.

According to yet another mode, the odor adsorption layer is layered on the gas barrier layer by extrusion coating. Before layering of the odor adsorption layer, a bonding layer made of an anchor coating agent may be provided beforehand on the layering surface of the gas barrier layer.

The anchor coating agent used may be any desired anchor coating agent suited for the purpose of use, and for example, an organic titanium-based, isocyanate-based, polyethylene-imine-based, acid-modified polyethylene-based or polybutadiene-based agent may be used.

Also, when the gas barrier layer comprises a thermoplastic resin, the resin composition for the gas barrier layer and the resin composition for the odor adsorption layer may be co-extruded to form a film, in order to produce the sheet of the invention.

<Moisture Absorption Layer>

According to the invention, a moisture absorption layer that adsorbs moisture may be provided in the pack, between the gas barrier layer and the odor adsorption layer. Such a moisture absorption layer may comprise, for example, a resin composition containing a moisture absorbent and a binder resin. The moisture absorbent is not particularly restricted, and there may be used a publicly known or commercially available material having a hygroscopic effect or humidifying effect.

A humidifying effect is an effect of absorbing moisture when the humidity is high and releasing moisture when the humidity is low, to maintain a constant humidity.

According to the invention, examples of substances that may be suitably used as moisture absorbents include silica gel, alumina gel, silica-alumina gel, anhydrous magnesium sulfate, zeolite, synthetic zeolite, calcium oxide, calcium chloride and dried alum, as well as mixtures thereof, although there is no limitation to these.

According to the invention, the binder resin mixed with the moisture absorbent is not particularly restricted so long as it can stably retain the moisture absorbent and does not adversely affect the odor-adsorbing effect of the invention, and any desired resin may be used. The resins mentioned above as heat-sealable resins to form the odor adsorption layer are particularly preferred for use.

By using these heat-sealable resins as binders, and layering the odor adsorption layer and moisture absorption layer in an adjacent manner, it is possible to obtain high interlayer adhesiveness, and to obtain high moisture absorption and humidifying effects. In addition, conducting film formation by co-extrusion of the odor adsorption layer and moisture absorption layer further increases these effects.

The amount of moisture absorbent added to the moisture absorption layer can exhibit a moisture absorption effect if it is present at 1 mass % or greater with respect to the total mass of the moisture absorption layer, and it is preferably present at 3 mass % or greater in order to obtain a satisfactory hygroscopic effect.

On the other hand, the amount of moisture absorbent added must be no greater than 50 mass % in order to obtain satisfactory film formability.

According to another mode, the moisture absorption layer may be a layer made of a hygroscopic resin such as nylon or ethylene-vinyl acetate copolymer. The moisture absorbent may also be added in an amount of up to 50 mass % in the hygroscopic resin.

The moisture absorption layer composed of a hygroscopic resin may be layered adjacent to the odor adsorption layer, similar to when it is composed of a resin composition containing a moisture absorbent and a binder resin (heat-sealable resin).

Also, while a film can be formed if the thickness of the moisture absorption layer is at least 5 µm, it is preferably 10 µm to 200 µm in order to obtain satisfactory film formability and hygroscopicity.

According to the invention, providing such a moisture absorption layer can remove moisture in the pack without interfering with the odor adsorbing effect of the odor adsorption layer, and prevent deterioration in quality of the contents. In addition, providing such a moisture absorption layer adjacent to the odor adsorption layer allows moisture that may pool in the odor adsorption layer to migrate to the moisture absorption layer, resulting in an even higher odor adsorbing effect.

<Package>

The PTP blister sheet of the invention is passed through a molding machine and subjected to PTP molding so that the surface on the odor adsorption layer side is the inner side of the pack. According to the invention, the PTP molding may be carried out by a commonly employed method, and vacuum forming, pressure forming or the like matching the shape of the contents to be packaged can form a blister on the sheet.

Contents such as a drug or food can be housed in the obtained molded article, and then a sealing material such as aluminum foil used to cover it, and heat sealed with the flange sections of the sheet, to allow production of a PTP blister pack of the invention. The method of heat sealing may be a publicly known method such as, for example, bar sealing, revolving roll sealing, belt sealing, impulse sealing, high-frequency sealing or ultrasonic sealing.

The pack is pressed at the blister to break the sealing material, to allow easy removal of the contents.

The pack of the invention may be used for packaging of various types of drugs or foods. In particular, it may be suitably used to package drugs and foods containing components that emit odors, and more specifically, substances that emit gases including carboxylic acid, hydrogen sulfide, mercaptane, ammonia, amine and aldehyde.

Example 1

There was prepared a resin composition including 3 mass % of an odor adsorption agent having a polyamine-derived amino group supported on silicon dioxide (NS-241: product of ToaGosei Co., Ltd., mean particle size: 3.5 μm), 3 mass % of an odor adsorption agent having a hydroxyl group supported on zirconium (NS-80E: product of ToaGosei Co., Ltd., mean particle size: 2 μm), and 3 mass % of an odor adsorption agent having a phosphate group supported on zirconium (NS-10: product of ToaGosei Co., Ltd., mean particle size: 1 μm), in LDPE (LC522: product of Japan Polyethylene Corp.).

A vinyl chloride (PVC)/vinylidene chloride (PVDC) composite sheet (F-9459: product of Mitsubishi Plastics, Inc., thickness: 240 μm) was coated with an anchor coat (A3210/A3075: product of Mitsui Chemical Polyurethane Co., Ltd., diluting solvent: ethyl acetate, dried coating amount: 0.3 g/m$^2$), and the resin composition was layered over it by extrusion coating to form an odor adsorption layer (thickness: 50 μm), and produce a PTP blister sheet of the invention having the multilayer structure: PVC-PVDC composite sheet/anchor coat layer/odor adsorption layer.

Example 2

A PTP blister sheet of the invention was produced in the same manner as Example 1, except that instead of LDPE in the heat-sealable resin composition used to form the odor adsorption layer, there was used polypropylene (WFX4: product of Japan Polypropylene Corp.).

Example 3

A PTP blister sheet of the invention having the multilayer structure: PVC•PVDC composite sheet/anchor coat layer/odor adsorption layer was produced in the same manner as Example 1, except that instead of the PVC-PVDC composite sheet F-9459 as the gas barrier film there was used the PVC•PVDC composite sheet F-9259 (product of Mitsubishi Plastics, Inc., thickness: 255 μm).

Example 4

A PTP blister sheet of the invention was produced in the same manner as Example 1, except that instead of the PVC•PVDC composite sheet as the gas barrier film there was used a PVC sheet (C-0471: product of Mitsubishi Plastics, Inc., thickness: 250 μm).

Example 5

A PTP blister sheet of the invention was produced in the same manner as Example 3, except that instead of LDPE in the heat-sealable resin composition used to form the odor adsorption layer, there was used polypropylene (WFX4: product of Japan Polypropylene Corp.).

Example 6

A resin composition was prepared including 3 mass % of NS-241 (product of ToaGosei Co., Ltd.), 3 mass % of NS-80E (product of ToaGosei Co., Ltd.) and 3 mass % of NS-10 (product of ToaGosei Co., Ltd.) in polypropylene (WFX4: product of Japan Polypropylene Corp.). This was subjected to co-extrusion film formation with polypropylene (WFX4: product of Japan Polypropylene Corp.), to produce a PTP blister sheet of the invention having the multilayer structure: polypropylene layer (thickness: 250 μm)/odor adsorption layer (thickness: 50 μm).

Example 7

A PTP blister sheet of the invention was produced in the same manner as Example 1, except that instead of the PVC-PVDC composite sheet as the gas barrier film there was used a polypropylene sheet (WFX4: product of Japan Polypropylene Corp. formed into a film with a thickness of 250 μm).

Example 8

A PET film (thickness: 12 μm, ESPET T4102, product of Toyobo, Ltd.) and an aluminum foil (thickness: 30 μm, product of Toyo Aluminium, KK.) were attached through a dry laminating bonding agent (RU004/H-1: product of Rock Paint Co., coating amount: 3.5 g/m$^2$ for each bonding layer, drying temperature: 70° C.), to produce a gas barrier film having the multilayer structure: PET film/bonding layer/aluminum foil.

A PTP blister sheet of the invention having the multilayer structure: PET film/bonding layer/aluminum foil/anchor coat layer/odor adsorption layer was produced in the same manner as Example 1, except that instead of a PVC•PVDC composite sheet as the gas barrier film there was used the gas barrier film produced as described above.

Example 9

A PTP blister sheet of the invention was produced in the same manner as Example 7, except that instead of LDPE in the heat-sealable resin composition used to form the odor adsorption layer, there was used polypropylene (WFX4: product of Japan Polypropylene Corp.).

Example 10

NS-241 (product of ToaGosei Co., Ltd.) and LDPE (LC522: product of Japan Polyethylene Corp.) were kneaded to prepare a resin composition containing 10 mass % of NS-241.

A PTP blister sheet of the invention was produced in the same manner as Example 1, except that this obtained resin composition was used as the resin composition to compose the odor adsorption layer.

Example 11

A PTP blister sheet of the invention was produced in the same manner as Example 9, except that instead of the PVC•PVDC composite sheet as the gas barrier film there was used a PVC sheet (C-0471: product of Mitsubishi Plastics, Inc., thickness: 250 μm).

Example 12

NS-80E (product of ToaGosei Co., Ltd.) and LDPE (LC522: product of Japan Polyethylene Corp.) were kneaded to prepare a resin composition containing 10 mass % of NS-80E.

A PTP blister sheet of the invention was produced in the same manner as Example 3, except that this obtained resin composition was used as the resin composition to compose the odor adsorption layer.

Example 13

NS-10 (product of ToaGosei Co., Ltd.) and LDPE (LC522: product of Japan Polyethylene Corp.) were kneaded to prepare a resin composition containing 10 mass % of NS-10.

A PTP blister sheet of the invention was produced in the same manner as Example 3, except that this obtained resin composition was used as the resin composition to compose the odor adsorption layer.

Example 14

NS-241 (product of ToaGosei Co., Ltd.) and LDPE (LC522: product of Japan Polyethylene Corp.) were kneaded to prepare a resin composition containing 10 mass % of NS-241.

Also, anhydrous magnesium sulfate (DRYKEEP S-KID: product of Sasaki Chemical Co., Ltd.) and LDPE (LC522: product of Japan Polyethylene Corp.) were kneaded to prepare a resin composition for formation of a moisture absorption layer containing 20 mass % of anhydrous magnesium sulfate.

A PVC sheet (C-0471: product of Mitsubishi Plastics, Inc., thickness: 250 μm) was coated with an anchor coat (A3210/A3075: product of Mitsui Chemical Polyurethane Co., Ltd., diluting solvent: ethyl acetate, dried coating amount: 0.3 g/m$^2$), and the aforementioned resin composition and a moisture absorption layer-forming resin composition were co-extruded over it by extrusion coating to produce a PTP blister sheet of the invention having the multilayer structure: PVC/anchor coat layer/moisture absorption layer/odor adsorption layer.

Example 15

A PTP blister sheet of the invention was produced in the same manner as Example 1, except that the addition amounts of NS-241 (product of ToaGosei Co., Ltd.), NS-80E (product of ToaGosei Co., Ltd.) and NS-10 (product of ToaGosei Co., Ltd.) in the resin composition were each 7 mass %.

Example 16

NS-241 (product of ToaGosei Co., Ltd.) and LDPE (LC522: product of Japan Polyethylene Corp.) were kneaded to prepare a resin composition containing 10 mass % of NS-241. The resin composition was formed into a film by an inflation method to obtain an odor adsorbing film with a thickness of 50 μm.

The obtained odor adsorbing film was attached to a PVC•PVDC composite sheet (F-9459: product of Mitsubishi Plastics, Inc., thickness: 240 μm) through a dry laminating bonding agent (RU004/H-1: product of Rock Paint Co., coating amount: 3.5 g/m$^2$ for each bonding layer, drying temperature: 70° C.), to produce a PTP blister sheet of the invention having the multilayer structure: PVC•PVDC composite sheet/bonding layer/odor adsorption layer.

Example 17

In the same manner as Example 1, a resin composition was prepared including 3 mass % of NS-241 (product of ToaGosei Co., Ltd.), 3 mass % of NS-80E (product of ToaGosei Co., Ltd.) and 3 mass % of NS-10 (product of ToaGosei Co., Ltd.) in LDPE (LC522: product of Japan Polyethylene Corp.). There was also prepared LDPE (LC522: product of Japan Polyethylene Corp.) containing no odor adsorption agent. Next, a resin composition including 9 mass % of an odor adsorption agent and LDPE containing no odor adsorption agent were co-extruded by extrusion coating to form a film, and an odor adsorbing film was formed having an odor adsorbing property in the intermediate layer and a total film thickness of 60 μm.

The obtained film was attached to a PVC•PVDC composite sheet (F-9459: product of Mitsubishi Plastics, Inc., thickness: 240 μm) and the odor adsorbing film through a dry laminating bonding agent (RU004/H-1: product of Rock Paint Co., coating amount: 3.5 g/m$^2$ for each bonding layer, drying temperature: 70° C.), to produce a PTP blister sheet of the invention having the multilayer structure: PVC-PVDC composite sheet/bonding layer/odor adsorbing film.

Example 18

Using a master batch having NS-241 (product of ToaGosei Co., Ltd., mean particle size: 3.5 μm) dispersed in LDPE with an MFR of 8 g/10 min (190° C.) at 10 mass %, and LLDPE (product of Prime Polymer Co., Ltd., EVOLUE SP2020, MFR: 2.3 g/10 min (190° C.)), they were mixed in a proportion of master batch/LLDPE=83.3/16.7 to prepare a resin composition for formation of an intermediate layer.

Also, using an anti-blocking agent (product of Sumitomo Chemical Co., Ltd., EMB-21, MFR: 5 g/10 min (190° C.), synthetic zeolite-containing) and LLDPE (product of Prime Polymer Co., Ltd., EVOLUE SP2020, MFR: 2.3 g/10 min (190° C.)), these were mixed in a proportion of anti-blocking agent/LLDPE=4/96, to prepare a thermoplastic resin for formation of an inner side thermoplastic resin layer.

The resin used for formation of the outer side thermoplastic resin layer was LLDPE (product of Prime Polymer Co., Ltd., EVOLUE SP2020, MFR: 2.3 g/10 min (190° C.)).

The resin composition and thermoplastic resin were used for 3-layer co-extrusion molding using an inflation method, to form an odor adsorbing film with a total film thickness of 50 μm, having an odor adsorbing property in the intermediate layer.

A PVC-PVDC composite sheet (F-9459: product of Mitsubishi Plastics, Inc., thickness: 240 μm) and the odor adsorbing film were attached through a dry laminating bonding agent (RU004/H-1: product of Rock Paint Co., coating amount: 3.5 g/m$^2$ for each bonding layer, drying temperature: 70° C.), to produce a PTP blister sheet of the invention having the multilayer structure: "PVC•PVDC composite sheet/bonding layer/odor adsorbing film".

Example 19

A PTP blister sheet of the invention was produced in the same manner as Example 18, except that the mixing ratio in the odor adsorbing film having an odor adsorbing property in the intermediate layer was: master batch/LLDPE=16.7/83.3.

Example 20

A PTP blister sheet of the invention was produced in the same manner as Example 18, except that the mixing ratio in the odor adsorbing film having an odor adsorbing property in the intermediate layer was: master batch/LLDPE=50/50.

Comparative Example 1

A PTP blister sheet was produced in the same manner as Example 1, except that instead of providing an odor adsorption layer, there was provided a sealant layer (thickness: 50 µm) comprising LDPE containing no odor adsorption agent (LC522: product of Japan Polyethylene Corp.).

Comparative Example 2

A PTP blister sheet was produced in the same manner as Example 1, except that the addition amounts of NS-241 (product of ToaGosei Co., Ltd.), NS-80E (product of Toa-Gosei Co., Ltd.) and NS-10 (product of ToaGosei Co., Ltd.) in the resin composition were each 12 mass %.

<Moldability>

The PTP blister sheets obtained in Examples 1 to 20 and Comparative Examples 1 and 2 were used for PTP molding with a blister pack molding machine (product of CKD), and the moldability was evaluated. The evaluation criteria were "G=Satisfactory molding possible without creasing during PTP molding" and "P=Satisfactory molding not possible due to considerable creasing during molding". The evaluation results are shown in Table 1.

<Film Formability>

The film appearance of the formed odor adsorption layer was observed and organoleptically evaluated. The evaluation criteria were as follows: "G=Film formation possible without producing wrinkles or bumps in film", and "P=Film formation difficult, with numerous wrinkles and bumps in film". The evaluation results are shown in Table 1.

<Deodorant Effect>

The PTP blister sheets produced in Examples 1 to 20 and Comparative Examples 1 and 2, cut out to 10 cm×10 cm, were placed in a 800 ml-volume sealed glass bottle together with odor components, and the change in odor after standing for 1 day was measured by an organoleptic evaluation. The odor components used were acetaldehyde, acetic acid or trimethylamine, all adjusted to 200 ppm.

The evaluation criteria for the organoleptic evaluation were as follows: "1=Odor unchanged from initial", "2=Odor slightly alleviated from initial", "3=Odor significantly alleviated compared to initial", "4=Absolutely no odor". The evaluation results are shown in Table 1.

TABLE 1

| | Evaluation results | | | | |
|---|---|---|---|---|---|
| | Film forma- bility [—] | Moldability [—] | Deodorant effect | | |
| | | | Acetal- dehyde | Acetic acid | Trimethylamine |
| Example 1 | G | G | 3 | 3 | 3 |
| Example 2 | G | G | 3 | 3 | 3 |
| Example 3 | G | G | 3 | 3 | 3 |
| Example 4 | G | G | 3 | 3 | 3 |
| Example 5 | G | G | 3 | 3 | 3 |
| Example 6 | G | G | 3 | 3 | 3 |
| Example 7 | G | G | 3 | 3 | 3 |
| Example 8 | G | G | 3 | 3 | 3 |
| Example 9 | G | G | 3 | 3 | 3 |
| Example 10 | G | G | 4 | 1 | 3 |
| Example 11 | G | G | 4 | 1 | 3 |
| Example 12 | G | G | 1 | 4 | 1 |
| Example 13 | G | G | 1 | 1 | 4 |
| Example 14 | G | G | 4 | 1 | 3 |
| Example 15 | G | G | 3 | 3 | 3 |
| Example 16 | G | G | 4 | 1 | 3 |
| Example 17 | G | G | 3 | 3 | 3 |
| Example 18 | G | G | 4 | 1 | 3 |
| Example 19 | G | G | 4 | 1 | 3 |
| Example 20 | G | G | 4 | 1 | 3 |
| Comp. Ex. 1 | G | G | 1 | 1 | 1 |
| Comp. Ex. 2 | P | — | — | — | — |

As clearly seen by the results, the packs of Examples 1 to 20 exhibited satisfactory film formability, moldability and deodorant effects.

EXPLANATION OF SYMBOLS

1. Gas barrier layer
2, 2a, 2b. Odor adsorption layers
3. Moisture absorption layer

The invention claimed is:

1. A PTP blister sheet comprising:
   a gas barrier layer;
   an odor adsorption layer including an outermost surface that faces the gas barrier layer and an innermost surface opposite to the outermost surface, the odor adsorption layer comprising a heat-sealable resin containing from 0.5% by mass to 30% by mass of an odor adsorption agent capable of bonding with an odorous substance, the odor adsorption agent being formed of a chemical adsorption agent supported on an inorganic porous body having a mean particle size of 0.01 µm to 10 µm; and
   a moisture absorption layer provided between the gas barrier layer and the odor adsorption layer, the moisture absorption layer containing a moisture absorbent and a binder resin, the moisture absorbent being at least one selected from the group consisting of zeolite, synthetic zeolite, and calcium oxide, and the moisture absorption layer being configured to adsorb moisture including adsorbing moisture from the odor adsorption layer, wherein the heat-sealable resin has a melt flow rate from 0.2 g/10 min to 4.0 g/10 as measured by a method according to JIS K7210, one of:
  the odor adsorption layer is an innermost layer of the PTP blister sheet, or
  the PTP blister sheet further comprises an inner layer that is the innermost layer of the PTP blister sheet, the inner layer comprising a heat-sealable resin that is a polyolefin-based resin, the chemical adsorption agent includes a reactive functional group for reacting with the odorous substance to bond the odorous substance to the odor adsorption agent, the chemical adsorption agent being at least one chemical adsorption agent selected from the group consisting of a compound having a hydroxyl group and a compound containing an amino group, and the odor adsorption layer has a concentration gradient of the odor adsorption agent from the innermost surface to the outermost surface such that the odor adsorption layer has different concentrations of the odor adsorption agent at the innermost surface and at the outermost surface.

2. A PTP blister pack comprising:
a PTP blister sheet according to claim 1.

3. The PTP blister sheet of claim 1, wherein the reactive functional group is a basic functional group.

4. The PTP blister sheet of claim 1, further comprising:
the inner layer, the inner layer being a fourth layer comprising the heat-sealable resin that is the polyolefin-based resin and no odor adsorption agent, and being adjacent to the odor adsorption layer,
wherein the gas barrier layer, odor adsorption layer, and moisture absorption layer, are a first layer, a second layer, and a third layer, respectively.

5. The PTP blister sheet of claim 4, further comprising:
a fifth layer comprising a heat-sealable resin and no odor adsorption agent, the fourth layer contacting the innermost surface of the odor adsorption layer, and the fifth layer contacting the outermost surface of the odor adsorption layer.

6. The PTP blister sheet of claim 1, wherein the concentration of the odor adsorption agent changes monotonically from the innermost surface to the outermost surface.

7. The PTP blister sheet of claim 6, wherein a lowest concentration of the odor adsorption agent in the odor adsorption layer is at the innermost surface.

8. The PTP blister sheet of claim 6, wherein a highest concentration of the odor adsorption agent in the odor adsorption layer is at the innermost surface.

* * * * *